United States Patent [19]

Okui et al.

[11] Patent Number: 6,054,607
[45] Date of Patent: Apr. 25, 2000

[54] PROCESS FOR THE PREPARATION OF CINNAMIC ACID ESTERS

[75] Inventors: Hideshi Okui; Yoshihisa Tsukamoto, both of Kusatsu; Shigeru Mio, Shiga-ken, all of Japan

[73] Assignee: Sankyo Company, Limited, Tokyo, Japan

[21] Appl. No.: 09/172,640

[22] Filed: Oct. 14, 1998

[30] Foreign Application Priority Data

Oct. 16, 1997 [JP] Japan ..................................... 9-283432

[51] Int. Cl.⁷ ..................................................... C07C 67/00
[52] U.S. Cl. ............................................................ 560/210
[58] Field of Search ............................................. 560/210

[56] References Cited

U.S. PATENT DOCUMENTS 4,618,698 10/1986 Beitzke .
5,359,122 10/1994 Huellmann et al. .
5,527,947 6/1996 Alexander et al. .

FOREIGN PATENT DOCUMENTS 0 165 521 12/1985 European Pat. Off. .
709227 8/1941 Germany .
61-7236 1/1986 Japan .

OTHER PUBLICATIONS

Marvel et al, "Ethly Cinnamate", *Organic Syntheses*, Collective vol. I, pp. 252–254 (1932).
Marvel et al "Ethyl Cinnamate", Organic Synthesis Coll., vol. 1, pp. 252–254.
A.d. Wissensch, "L. Claisen: Zur Darstellung der Zimmtsäure und ihrer Homologen", Ber., 23, pp. 976–978 (1890).
Gurjar et al. (Indian J. Chemistry; Section B; 14B(7); pp. 548–549), 1976.

*Primary Examiner*—Gary Geist
*Assistant Examiner*—Robert W. Deemie
*Attorney, Agent, or Firm*—Frishauf, Holtz, Goodman, Langer & Chick, P.C.

[57] ABSTRACT

A process for the preparation of a cinnamic acid ester comprises condensing a benzaldehyde with an acetic acid ester in the presence of a base. The reaction mixture is then treated, without adding an additional solvent or after adding an additional solvent, with an acid to convert a 3-alkoxy-3-phenylpropionic acid ester in the reaction mixture into a corresponding cinnamic acid ester. This procedure allows cinnamic acid ester derivatives of high-purity to be obtained in good yield.

20 Claims, No Drawings

PROCESS FOR THE PREPARATION OF CINNAMIC ACID ESTERS

BACKGROUND OF THE INVENTION

1. Field of the Invention

This invention relates to a process for the preparation of cinnamic acid esters. Cinnamic acid derivatives are useful as antioxidants and ultraviolet absorbers in plastics. They are also useful as intermediates in the synthesis of medicines, agricultural chemicals and perfumes.

2. Background Information

A process for preparing a cinnamic acid ester by the condensation of a benzaldehyde with an acetic acid ester is known as the Claisen-Schmidt reaction [Ber., 23, 976 (1890)]. When the Claisen-Schmidt reaction is effected in the presence of sodium, however, the Cannizzaro reaction occurs preferentially, to give benzyl alcohol as the main product and to afford a cinnamic acid ester, which is the desired product, in a low yield.

German Patent DE709227 describes a process for preparing ethyl cinnamate or methyl cinnamate by a condensation reaction between a benzaldehyde and an ethyl or methyl acetate in the presence of sodium hydride as a base. Sodium hydride, however, is not easy to handle and is expensive and so that there is a demand to improve this process.

In Org. Synth. Coll., Vol. 1, 252, a process for preparing ethyl cinnamate by condensing benzaldehyde and ethyl acetate in the presence of a small amount of ethanol using finely dispersed sodium as a base is described. This procedure is not industrially acceptable, because sodium cannot easily be handled and besides, the yield of this process is not sufficiently high, specifically, it is generally between 68 and 74%.

Japanese Patent Application Kokai Sho 61-7236 describes a process for preparing a cinnamic acid ester by a condensation reaction between a benzaldehyde and an acetic acid ester, using an alcoholic solution of a metal alkoxide as a base. This procedure, however, requires a specific purification step, such as distillation, in order to isolate the cinnamic acid ester from the reaction mixture, because 3-methoxy-3-phenylpropionic acid is produced as a by-product in an amount of between 4.7 and 12.5%. This procedure is therefore associated with several problems, such as lower yields, troublesome purification and treatment of by-products.

U.S. Pat. No. 4,618,698 describes a process for the preparation of an optionally substituted cinnamic acid by reacting an optionally substituted benzaldehyde with an optionally substituted acetic acid ester with an alcoholate in the presence of an alcohol to form a mixture of an optionally substituted cinnamic acid ester and a β-alkoxy-β-phenylpropionic acid, and then hydrolysing the mixture under acidic or basic conditions to give an optionally substituted cinnamic acid. This optionally substituted cinnamic acid then needs to be esterified to give the desired optionally substituted cinnamic acid ester.

U.S. Pat. No. 5,359,122 describes a process for preparing, inter alia, an optionally substituted cinnamic acid or ester thereof by reacting a dialkyl acetal of an aromatic aldehyde with ketene in the presence of a catalytic amount of a protic or Lewis acid to give a 3-arylpropionic acid derivative, which is then reacted with an acid or base in the presence of an alkanol to give the desired optionally substituted cinnamic acid or ester.

BRIEF SUMMARY OF THE INVENTION

As a result of an extensive investigation of the synthesis of cinnamic acid esters, the present inventors have discovered a process for preparing high-purity cinnamic acid esters in good yields, which process provides an industrially feasible preparation method.

The present invention provides a process for the preparation of cinnamic acid esters of formula (III):

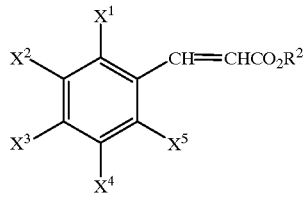

(III)

[wherein:

$X^1$, $X^2$, $X^3$, $X^4$ and $X^5$ are the same as or different from each other and each represents a hydrogen atom, an alkyl group having from 1 to 6 carbon atoms, a cycloalkyl group having from 3 to 6 carbon atoms, a halogen atom, an alkoxy group having from 1 to 6 carbon atoms, a haloalkyl group having from 1 to 6 carbon atoms, a haloalkoxy group having from 1 to 6 carbon atoms, an alkylthio group having from 1 to 6 carbon atoms, an alkylsulfinyl group having from 1 to 6 carbon atoms, an alkylsulfonyl group having from 1 to 6 carbon atoms, a nitro group, a cyano group, a phenyl group, a phenoxy group, an amino group, an alkylamino group having from 1 to 6 carbon atoms or a dialkylamino group having from 1 to 6 carbon atoms in each alkyl part, or any two adjacent substituents represented by $X^1$, $X^2$, $X^3$, $X^4$ and $X^5$ may form a 5- or 6-membered saturated or unsaturated ring which may contain from one to four hetero-atoms selected from the group consisting of oxygen atoms, nitrogen atoms and sulfur atoms; and $R^2$ represents an alkyl group having from 1 to 6 carbon atoms or a cycloalkyl group having from 3 to 6 carbon atoms], which process comprises reacting, in the presence of a base, a benzaldehyde of formula (I):

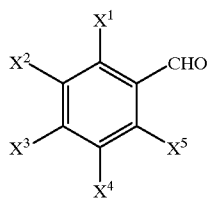

(I)

[wherein $X^1$, $X^2$, $X^3$, $X^4$ and $X^5$ are as defined above] with an acetic acid ester of formula (II):

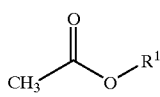

(II)

[wherein $R^1$ represents an alkyl group having from 1 to 6 carbon atoms or a cycloalkyl group having from 3 to 6 carbon atoms], and treating the reaction mixture, without adding an additional solvent or after adding an additional solvent, with an acid to convert a 3-alkoxy-3-phenylpropionic acid ester of formula (IV):

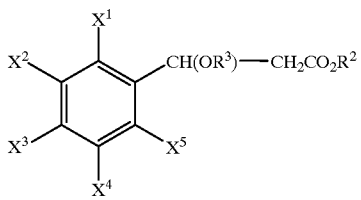

(IV)

[wherein $X^1$, $X^2$, $X^3$, $X^4$, $X^5$ and $R^2$ are as defined above and $R^3$ represents an alkyl group having from 1 to 6 carbon atoms or a cycloalkyl group having from 3 to 6 carbon atoms] which is present in the reaction mixture into a cinnamic acid ester of formula (III).

DETAILED DESCRIPTION OF THE INVENTION

Where $R^1$, $R^2$, $R^3$, $X^1$, $X^2$, $X^3$, $X^4$ or $X^5$ represents an alkyl group having from 1 to 6 carbon atoms, this may be straight or branched chain group. Examples of such alkyl groups include the methyl, ethyl, propyl, isopropyl, butyl, isobutyl, sec-butyl, t-butyl, pentyl, isopentyl, 2-methylbutyl, neopentyl, t-pentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups, of which straight or branched chain alkyl groups having from 1 to 3 carbon atoms are preferred and the methyl and ethyl groups are more preferred.

Where $R^1$, $R^2$, $R^3$, $X^1$, $X^2$, $X^3$, $X^4$ or $X^5$ represents a cycloalkyl group, this has from 3 to 6 carbon atoms in a saturated carbocyclic ring, and examples are the cyclopropyl, cyclobutyl, cyclopentyl and cyclohexyl groups.

Where $X^1$, $X^2$, $X^3$, $X^4$ or $X^5$ represents a halogen atom, this may be, for example, a fluorine, chlorine, bromine or iodine atom, of which the fluorine and chlorine atoms are preferred.

Where $X^1$, $X^2$, $X^3$, $X^4$ or $X^5$ represents an alkoxy group having from 1 to 6 carbon atoms, this may be straight or branched chain group. Examples of such alkoxy groups include the methoxy, ethoxy, propoxy, isopropoxy, butoxy, isobutoxy, sec-butoxy, t-butoxy, pentyloxy, isopentyloxy, 2-methylbutoxy, neopentyloxy, 1-ethylpropoxy, hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy and 2-ethylbutoxy groups, of which those straight or branched chain alkoxy groups having from 1 to 3 carbon atoms are preferred and the methoxy group is more preferred.

Where $X^1$, $X^2$, $X^3$, $X^4$ or $X^5$ represents a haloalkyl group having from 1 to 6 carbon atoms, this may be any of the alkyl groups having from 1 to 6 carbon atoms exemplified above, which is substituted by from one to three of the halogen atoms exemplified above, of which the above-exemplified alkyl groups having from 1 to 3 carbon atoms substituted by from one to three fluorine or chlorine atoms are preferred and the chloromethyl and trifluoromethyl groups are more preferred.

Where $X^1$, $X^2$, $X^3$, $X^4$ or $X^5$ represents a haloalkoxy group having from 1 to 6 carbon atoms, this may be any of the alkoxy groups having from 1 to 6 carbon atoms exemplified above, which is substituted by from one to three of the halogen atoms exemplified above, of which the above-exemplified alkoxy groups having from 1 to 3 carbon atoms substituted by from one to three fluorine or chlorine atoms are preferred and the chloromethoxy and trifluoromethoxy groups are more preferred.

Where $X^1$, $X^2$, $X^3$, $X^4$ or $X^5$ represents an alkylthio group having from 1 to 6 carbon atoms, the alkyl part of this may be any of the alkyl groups having from 1 to 6 carbon atoms exemplified above, of which the straight or branched chain alkyl groups having from 1 to 3 carbon atoms are preferred. Of these, the methylthio group is more preferred.

Where $X^1$, $X^2$, $X^3$, $X^4$ or $X^5$ represents an alkylsulfinyl group having from 1 to 6 carbon atoms, the alkyl part of this may be any of the alkyl groups having from 1 to 6 carbon atoms exemplified above, of which the straight or branched chain alkyl groups having from 1 to 3 carbon atoms are preferred. Of these, the methylsulfinyl group is more preferred.

Where $X^1$, $X^2$, $X^3$, $X^4$ or $X^5$ represents an alkylsulfonyl group having from 1 to 6 carbon atoms, the alkyl part of this may be any of the alkyl groups having from 1 to 6 carbon atoms exemplified above, of which the straight or branched chain alkyl groups having from 1 to 3 carbon atoms are preferred. Of these, the methylsulfonyl group is more preferred.

Where any adjacent two of $X^1$, $X^2$, $X^3$, $X^4$ and $X^5$, together with the two carbon atoms to which they are attached, represent a 5- or 6-membered saturated or unsaturated heterocyclic ring, this may contain from one to four hetero-atoms selected from the group consisting of oxygen, nitrogen and sulfur atoms. Where there are four, three or two hetero-atoms, we prefer that 0, 1 or 2 of these should be sulfur and/or oxygen atoms and that correspondingly 4, 3 or 2 or 3, 2 or 1 or 2, 1 or 0 should be nitrogen atoms. Examples of such heterocyclic groups include such 5- or 6-membered rings as furan, pyrrole, thiophene, pyridine, dihydropyran, dihydropyrrole, pyrazole and pyrimidine, of which furan is preferred.

The process of the present invention for the preparation of cinnamic acid esters is shown in the following reaction scheme:

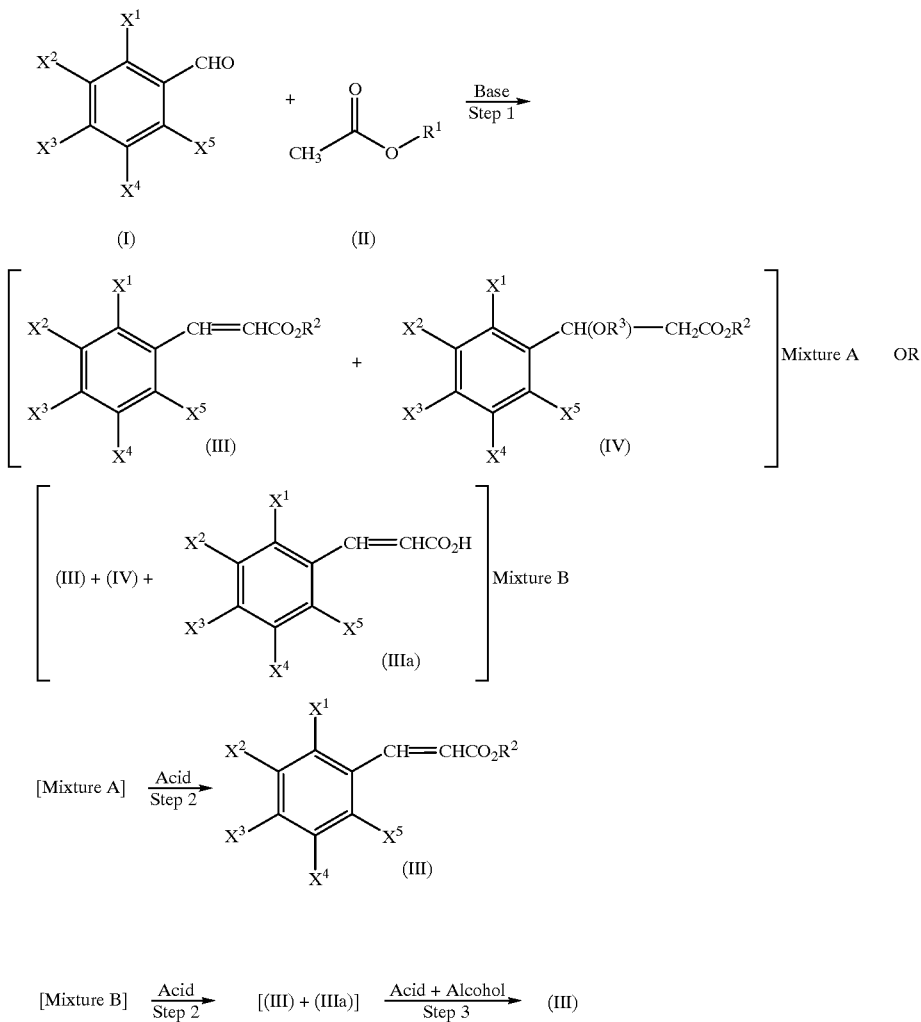

wherein $X^1$, $X^2$, $X^3$, $X^4$, $X^5$, $R^1$, $R^2$ and $R^3$ are as defined above.

Step 1

In this step, a benzaldehyde of formula (I) is condensed with an acetic acid ester of formula (II) in the presence of a base to give a mixture of a cinnamic acid ester of formula (III) and a 3-alkoxy-3-phenylpropionic acid ester of formula (IV).

Examples of the acetic acid ester include methyl, ethyl and propyl acetate, of which methyl and ethyl acetate are preferred.

The acetic acid ester is ordinarily used in an amount of about 0.5 equivalent or in a large excess relative to the benzaldehyde used. From 2 to 10 equivalents of the acetic acid ester are preferred per equivalent of the benzaldehyde.

The base which is used in this reaction of the present invention is preferably a metal alkoxide of formula (V):

$$R^4OM \qquad (V)$$

wherein $R^4$ represents an alkyl group having from 1 to 6 carbon atoms and

M represents an alkali metal.

Examples of such metal alkoxides include alkali metal salts of lower alcohols, such as sodium methoxide, sodium ethoxide and potassium t-butoxide. Of these, the sodium alkoxides are more preferred, sodium methoxide and sodium ethoxide are still more preferred, and sodium methoxide is most preferred.

The base may be employed in the form of an anhydrous powder or as a solution in the corresponding alcohol of formula $R^4OH$.

The metal alkoxide is ordinarily used in an amount of from 0.5 to 10 equivalents, preferably from 1 to 2 equivalents, relative to the benzaldehyde.

The reaction in this step can be carried out in the acetate ester which is used in the reaction or in another solvent, however, we prefer to use the alkyl acetate. If another solvent is used in this reaction, there is no particular limitation on its nature, provided that it can dissolve the reagents, at least to some extent, and that it has no adverse effect on the reaction. Examples of suitable solvents include: aliphatic hydrocarbons, such as hexane and petroleum ether; aromatic hydrocarbons, such as benzene and toluene; ethers, such as diethyl ether and tetrahydrofuran; and amides, such as dimethylformamide, of which the aliphatic hydrocarbons and aromatic hydrocarbons are preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −70° C. to 150° C., more preferably from −20° C. to 80° C. The time required for the reaction may also vary widely, depending on many factors, notably the reaction temperature and the nature of the reagents, base and solvent employed. However, provided that the reaction is effected under the preferred conditions outlined above, a period of from 30 minutes to 48 hours, more preferably from 1 hour to 24 hours, will usually suffice.

$R^2$ of the compound of formula (III) and (IV) and $R^3$ of the compound of formula (IV) can be derived both from $R^1$ of the compound of formula (II) and $R^4$ of the compound of formula $R^4OM$ when $R^4OM$ is used as the base. The proportions of $R^1$ and $R^4$ in the final product can vary depending upon the reaction conditions.

Step2

In this step, the cinnamic acid ester of formula (III) is obtained by treating a mixture of the cinnamic acid ester of formula (III) and the 3-alkoxy-3-phenylpropionic acid ester of formula (IV) with an acid.

There is no particular limitation on the nature of the acid provided that its pH is not higher than 6. Examples include sulfonic acids, such as methanesulfonic acid and p-toluenesulfonic acid; carboxylic acids, such as formic acid, acetic acid and trifluoroacetic acid; mineral acids, such as hydrochloric acid, sulfuric acid and perchloric acid; and Lewis acids, such as aluminum chloride and zinc chloride. Of these, hydrochloric acid and sulfuric acid are preferred.

The acid is generally used in an amount of from 0.1 to 20 equivalents, preferably from 0.5 to 5 equivalents per equivalent of the 3-alkoxy-3-phenylpropionic acid ester.

This step can be performed without purifying the reaction mixture prepared in Step 1 or after purifying it; and without adding an additional solvent or after adding an additional solvent.

Where an additional solvent is employed, there is no particular restriction on the nature of the solvent, provided that it has no adverse effect on the reaction or on the reagents involved and that it can dissolve the reagents, at least to some extent. Examples of suitable solvents include: aliphatic hydrocarbons, such as hexane; aromatic hydrocarbons, such as benzene and toluene; ethers, such as diethyl ether and tetrahydrofuran; and amides, such as dimethylformamide. Of these, the aliphatic and aromatic hydrocarbons are preferred.

We have found that, where this step, like the corresponding step of U.S. Pat. No. 5,359,122 is effected in an alcohol as solvent, the yields are relatively low. Accordingly, it is strongly preferred that the second step of the process of the present invention should be carried out in the absence of any added alcohol.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0 to 150° C., more preferably from 50 to 120° C. The time required for the reaction may also vary widely, depending on many factors, notably the reaction temperature and the nature of the reagents, base and solvent employed. However, provided that the reaction is effected under the preferred conditions outlined above, a period of from 30 minutes to 48 hours, more preferably from 1 to 24 hours, will usually suffice.

After completion of the above steps, the reaction product may be isolated from the reaction mixture by a conventional method. For example, the desired compound can be isolated by adding a water-immiscible organic solvent (such as ethyl acetate) to the reaction mixture, washing (for example with a mixture of ice and water, with a saturated sodium hydrogencarbonate solution, with water or with a saturated aqueous solution of sodium chloride or a combination thereof), drying over a desiccant such as anhydrous sodium sulfate and then distilling off the solvent under reduced pressure. The desired compound can, if necessary, be further purified by a known method such as distillation.

Step 3

In some cases, a significant amount of a cinnamic acid of formula (IIIa) [i.e. a compound of formula (III) in which $R^2$ represents a hydrogen atom] may be formed as a by-product. In this case, a third optional step may be carried out in order to convert the cinnamic acid to an ester of formula (III), by reacting the cinnamic acid of formula (IIIa) with an alcohol in the presence of an acid.

The nature of the alcohol will, of course, depend on the nature of the group represented by $R^2$ which it is desired to introduce. Examples include methanol, ethanol, propanol and butanol, of which methanol and ethanol are preferred.

There is likewise no particular restriction on the nature of the acids used, and any acid commonly used in reactions of this type may equally be used here, provided that it can maintain a pH of no more than 6 in the reaction mixture. Examples of such acids include: sulfonic acids, such as methanesulfonic acid and p-toluenesulfonic acid; carboxylic acids, such as formic acid, acetic acid and trifluoroacetic acid; mineral acids, such as hydrochloric acid, sulfuric acid and perchloric acid; and Lewis acids, such as aluminum chloride and zinc chloride. Of these, hydrochloric acid and sulfuric acid are preferred.

The acid is generally used in an amount of from 0.01 to 1.00 weight percent, preferably from 0.1 to 10 weight percent, based on the weight of the crude mixture obtained in Step 2.

This step can be performed without purifying the reaction mixture prepared in Step 2 or after purifying it; and without adding an additional solvent or after adding an additional solvent.

Where an additional solvent is employed, there is no particular restriction on the nature of the solvent, provided that it has no adverse effect on the reaction or on the reagents involved and that it can dissolve the reagents, at least to some extent. Examples of suitable solvents include: aliphatic hydrocarbons, such as hexane and methylcyclohexane; aromatic hydrocarbons, such as benzene and toluene; ethers, such as diethyl ether and tetrahydrofuran; and amides, such as dimethylformamide. Of these, the aliphatic and aromatic hydrocarbons are preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 150° C., more preferably from 50° C. to 120° C. The time required for the reaction may also vary widely, depending on many factors, notably the reaction temperature and the nature of the reagents, acid and solvent employed. However, provided that the reaction is effected under the preferred conditions outlined above, a period of from 30 minutes to 48 hours, more preferably from 1 to 24 hours, will usually suffice.

Steps 2 and 3 can be performed in one pot.

After completion of the above steps, the reaction product may be isolated from the reaction mixture by a conventional method. For example, the desired compound can be isolated by adding a water-immiscible organic solvent (such as toluene) and an acid to the reaction mixture, separating the organic layer and then distilling off the solvent under reduced pressure. The desired compound can, if necessary, be further purified by a known method such as distillation.

In some cases, however, the amount of cinnamic acid produced as a by-product is negligible, in which case Step 3 may be omitted.

The present invention will hereafter be described in greater detail by reference to the following non-limiting Examples.

EXAMPLE 1

Methyl cinnamate 1.22 g of sodium cut into pieces were added, whilst stirring, to 20 ml of anhydrous methanol. After the sodium had dissolved, the methanol was distilled off under reduced pressure. 16.3 ml of anhydrous methyl acetate were then added dropwise to the resulting sodium methoxide, while maintaining the temperature at from −20° C. to −10° C. under a nitrogen gas atmosphere. 4.5 g of benzaldehyde were then added dropwise while maintaining the temperature at from −15° C. to −10° C. After completion of the dropwise addition, the reaction mixture was stirred at −10° C. for 20 minutes and then at room temperature for 3 hours. At the end of this time, 6 ml of acetic acid were added to the reaction mixture. The mixture was then stirred, after which it was allowed to stand overnight at room temperature. The reaction mixture was then heated at 60° C. for 2 hours, after which 20 ml of water and 10 ml of ethyl acetate were added, followed by stirring for 10 minutes. The organic layer was separated and the aqueous layer was extracted three times, each time with 20 ml of ethyl acetate. The organic layer and extracts were combined, washed with a saturated aqueous solution of sodium hydrogencarbonate, water and a saturated aqueous solution of sodium chloride, in that order, after which it was dried over anhydrous sodium sulfate. The solvent was then removed by distillation under reduced pressure, to give an oil (6.80 g). The resulting oil was distilled (at 6 mmHg and 105 to 120° C.), to obtain 5.85 g of a mixture of methyl cinnamate and methyl 3-methoxy-3-phenylpropionate. The mixture contained 16 mol % of methyl 3-methoxy-3-phenylpropionate.

5 ml of anhydrous toluene and one drop of concentrated sulfuric acid were added, in that order, to 1.00 g of the resulting mixture of methyl cinnamate and methyl 3-methoxy-3-phenylpropionate. The resulting mixture was heated under reflux for 6.5 hours. At the end of this time, the reaction mixture was allowed to cool, after which 30 ml of ethyl acetate were added, and the mixture was washed with water and with a saturated aqueous solution of sodium chloride, in that order. The mixture was dried over anhydrous sodium sulfate, and then the solvent was removed by distillation under reduced pressure, to afford 0.961 g of methyl cinnamate (purity: 98.7%; yield: 81.7%).

$^1$H-Nuclear Magnetic Resonance (200 MHz, CDCl$_3$), δ(ppm):

7.71 (1H, doublet, J=16.0 Hz);
7.57–7.52 (2H, multiplet);
7.43–7.38 (3H, multiplet);
6.46 (1H, doublet, J=16.0 Hz);
3.82 (3H, singlet).

EXAMPLE 2

Methyl cinnamate 16.0 ml of anhydrous methyl acetate were added dropwise to 3.62 g of sodium methoxide (content: at least 95%), while maintaining the temperature at −10° C. to −8° C., after which 4.50 g of benzaldehyde were added dropwise, while maintaining the temperature at −8° C. to −2° C. After completion of the dropwise addition, the reaction mixture was stirred at −5 to −3° C. for 20 minutes and then at room temperature for 3 hours. At the end of this time, dilute aqueous sulfuric acid (prepared from 3.50 g of concentrated sulfuric acid and 20 ml of water) was added to the reaction mixture, whilst ice cooling, and then the mixture was stirred for one hour whilst ice cooling and then for three hours at room temperature. After the reaction mixture had been allowed to stand overnight, 20 ml of water and 40 ml of ethyl acetate were added. The organic layer was then separated and the aqueous layer was extracted three times, each time with 20 ml of ethyl acetate. The organic layer and extracts were combined, washed with a saturated aqueous solution of sodium hydrogencarbonate, with water and with a saturated aqueous solution of sodium chloride, in that order, and then dried over anhydrous sodium sulfate. The solvent was removed by distillation under reduced pressure, to give 7.44 g of an oil. The oil contained 7 mol % of methyl 3-methoxy-3-phenylpropionate.

20 ml of toluene were added to the oil, and the solvent was evaporated removed by evaporation under reduced pressure. 35 ml of anhydrous toluene and one drop of concentrated sulfuric acid were added to the residue, and then the mixture was heated under reflux for 4.5 hours. Four drops of concentrated sulfuric acid were then added, and the resulting mixture was heated under reflux for 3 hours, followed by the addition of two drops of concentrated sulfuric acid and further heating under reflux for 5.5 hours. At the end of this time, the reaction mixture was allowed to cool down, and then 50 ml of toluene were added. The resulting mixture was washed with water, with a saturated aqueous solution of sodium hydrogencarbonate, with water and with a saturated aqueous solution of sodium chloride, in that order, and then dried over anhydrous sodium sulfate. The solvent was removed by distillation under reduced pressure, to afford 6.08 g of methyl cinnamate (purity: 98.1%; yield: 86.8%).

EXAMPLE 3

Methyl cinnamate 160 ml of anhydrous methyl acetate were added dropwise to 36.3 g of sodium methoxide (content: at least 95%), while maintaining the temperature at −16 to −13° C., followed by the dropwise addition of 45.2 g of benzaldehyde while maintaining the temperature at −18° C. to −5° C. After completion of the dropwise addition, the reaction mixture was stirred at −5 to −14° C. for 20 minutes and then at room temperature for 3 hours. Diluted aqueous sulfuric acid and ice (prepared from 3.50 g of concentrated sulfuric acid and 400 g of ice) were added, whilst ice-cooling, to the reaction mixture, and then the mixture was stirred, whilst ice-cooling for 30 minutes and at room temperature for one hour. The organic layer was then separated from the reaction mixture. 400 ml of water were added to the aqueous layer, and the mixture was extracted three times, each time with 100 ml of ethyl acetate. The organic layer and the extracts were combined, washed with a saturated aqueous solution of sodium hydrogencarbonate, with water, with a saturated aqueous solution of sodium hydrogencarbonate, with water and with a saturated aqueous solution of sodium chloride, in that order, and then dried over anhydrous sodium sulfate. The solvent was removed by distillation under reduced pressure, to give an oil (83.5 g). The resulting oil was distilled (at 6 mmHg and 110 to 140° C.), to obtain 63.2 g of a mixture containing methyl cinnamate and methyl 3-methoxy-3-phenylpropionate. The mixture contained 9 mol % of methyl 3-methoxy-3-phenylpropionate.

350 ml of anhydrous toluene and then 0.50 g of concentrated sulfuric acid were added to the oil. The resulting mixture was heated under reflux for 5 hours. A further 0.50 g of concentrated sulfuric acid was added to the reaction mixture, and then the mixture was heated under reflux for 2.5 hours. At the end of this time, a further 1.00 g of concentrated sulfuric acid was added, and the mixture was heated under reflux for 3.5 hours. The mixture was cooled, and then 200 ml of toluene were added to the reaction mixture. The resulting mixture was washed with ice-water, with a saturated aqueous solution of sodium hydrogencarbonate, with water and with a saturated aqueous solution of sodium chloride, in that order, after which it was dried over anhydrous sodium sulfate. The solvent was then removed by distillation under reduced pressure, to afford 62.2 g (purity: 6.5%; yield: 87.0%) of the title compound.

EXAMPLE 4

Methyl cinnamate

A two-necked 3-liter flask was equipped with a thermometer and a 1-liter dropping funnel and purged with nitrogen gas. 125.10 g (2.20 mol) of sodium methoxide (special class reagent, content: at least 95%) were charged into the flask. After the flask had been cooled to an internal temperature of 0° C. in an ice-water-salt bath, 747.0 ml of methyl acetate were added dropwise, while maintaining the internal temperature at 10° C. or lower. While again cooling in the ice-water-salt bath, 203.3 ml of benzaldehyde were added dropwise over 60 minutes at such a rate that the internal temperature did not exceed 25° C. The flask was then removed from the cooling bath, and the reaction mixture was stirred at room temperature for 3 hours. At the end of this time, a mixture of 600 ml of 4 N aqueous hydrochloric acid and 500 ml of methanol was added to the reaction mixture at room temperature to dissolve the precipitate. The resulting solution was extracted three times, each time with 1.5 liters of methyl acetate. The extract was washed twice with a saturated aqueous solution of sodium chloride, dried over anhydrous magnesium sulfate and then concentrated by evaporation under reduced pressure, to give a reddish brown oil. The oil contained 11 mol % of methyl 3-methoxy-3-phenylpropionate.

The oil was dissolved in 1.0 liter of anhydrous toluene. 10.70 ml of concentrated sulfuric acid were added at room temperature to the resulting solution, and then the mixture was heated under reflux for 3 hours. At the end of this time, the reaction mixture was allowed to cool down, and then 81.0 ml of methanol and 10.7 ml of concentrated sulfuric acid were added. The resulting mixture was heated under reflux for further two hours, after which the reaction mixture was allowed to cool down. The reaction mixture was then washed twice with a saturated aqueous solution of sodium chloride, dried over anhydrous magnesium sulfate and then concentrated by evaporation under reduced pressure, to obtain a brown oil. The resulting oil was distilled under reduced pressure (at 4 mmHg, 103 to 106° C.), to afford 297.78 g (purity: 98.9%; yield: 91.8%) of methyl cinnamate.

EXAMPLE 5

Methyl cinnamate and ethyl cinnamate 188 ml of ethyl acetate were added dropwise, while maintaining the temperature at 5° C., to 29.47 ml of sodium methoxide (content at least 95%), and then 50.00 g of benzaldehyde were added dropwise to the mixture, while maintaining the temperature at 20–25° C. After the addition was complete, the reaction mixture was stirred at 25° C. for 2 hours. 53.00 g of 35% aqueous hydrochloric acid, 150 ml of water and 200 ml of toluene were then added, and the mixture was stirred at 20–25° C. for 30 minutes. The organic layer was then separated and concentrated by evaporation under reduced pressure, to give a crude oil (92.96 g).

250 ml of toluene and 2.5 ml of 97% sulfuric acid were added to the resulting oil, and the mixture was heated under reflux for 3 hours. 2.5 ml of 97% sulfuric acid and 50 ml of methanol were added to the resulting mixture, and the mixture was again heated under reflux for 3 hours. At the end of this time, the mixture was cooled, 200 ml of water were added, and the mixture was stirred vigorously. The organic layer was then separated and concentrated by evaporation under reduced pressure, to give an oil (87.45 g), which was then distilled (at 4 mmHg, 103–110° C.), to afford a mixture of methyl cinnamate and ethyl cinnamate (purities: methyl cinnamate 61.76%; ethyl cinnamate 36.75%; total yield 97.5%).

EXAMPLE 6

Methyl cinnamate 136.80 g of ethyl acetate were added at 60° C. to a mixture of 98.00 g of sodium methoxide (content 28%) and 100 ml of toluene. 50.00 g of benzaldehyde were then added, while maintaining the temperature at 60° C. When the addition was complete, the reaction mixture was stirred, while heating under reflux, for 5.5 hours. The reaction mixture was then cooled, after which 53.00 g of 35% aqueous hydrochloric acid, 150 ml of water and 100 ml of toluene were added. The mixture was then stirred at 20–25° C. for 20 minutes. The organic layer was then separated and concentrated by evaporation under reduced pressure, to give a crude oil (78.49 g). The oil contained 13.8 mol % of methyl 3-methoxy-3-phenylpropionate and 8.7 mol % of cinnamic acid as a by-product.

250 ml of toluene and 2.5 ml of 97% sulfuric acid were added to the resulting oil, and the mixture was heated under reflux for 3.5 hours. 2.5 ml of 97% sulfuric acid and 50 ml of methanol were added to the resulting mixture, and the mixture was again heated under reflux for 2.5 hours. At the end of this time, the mixture was cooled, 200 ml of water were added, and the mixture was stirred vigorously. The organic layer was then separated and concentrated by evaporation under reduced pressure, to give an oil (72.90 g), which contained 91.0% of methyl cinnamate (yield 88.6%).

Cinnamic acid ester derivatives of high purity can be obtained in good yields by the above procedure. The present invention provides an industrially feasible method of preparing cinnamic acid ester derivatives that are useful as antioxidants and as ultraviolet absorbers for plastics, and as intermediates for the synthesis of medicines, agricultural chemicals and perfumes.

We claim:
1. A process for the preparation of a cinnamic acid ester of a formula (III):

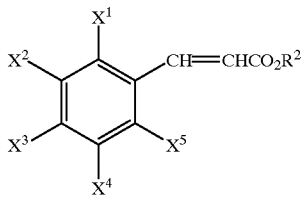
(III)

wherein:
X$^1$, X$^2$, X$^3$, X$^4$ and X$^5$ are the same as or different from each other and each represents a hydrogen atom, an alkyl group having from 1 to 6 carbon atoms, a cycloalkyl group having from 3 to 6 carbon atoms, a halogen atom, an alkoxy group having from 1 to 6 carbon atoms, a haloalkyl group having from 1 to 6 carbon atoms, a haloalkoxy group having from 1 to 6 carbon atoms, an alkylthio group having from 1 to 6 carbon atoms, an alkylsulfinyl group having from 1 to 6 carbon atoms, an alkylsulfonyl group having from 1 to 6 carbon atoms, a nitro group, a cyano group, a phenyl group, a phenoxy group, an amino group, an alkylamino group having from 1 to 6 carbon atoms or a dialkylamino group having from 1 to 6 carbon atoms in each alkyl part, or any two adjacent substituents represented by X$^1$, X$^2$, X$^3$, X$^4$ and X$^5$ form a 5- or 6-membered saturated or unsaturated ring which optionally contains from one to four hetero-atoms selected from the group consisting of oxygen atoms, nitrogen atoms and sulfur atoms; and R$^2$ represents an alkyl group having from 1 to 6 carbon atoms or a cycloalkyl group having from 3 to 6 carbon atoms, which process comprises:
(a) reacting, in the presence of a base, a benzaldehyde of formula (I):

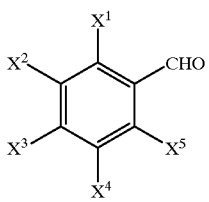
(I)

wherein
X$^1$, X$^2$, X$^3$, X$^4$ and X$^5$ are as defined above, with an acetic acid ester of a formula (II):

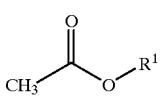
(II)

wherein
R$^1$ represents an alkyl group having from 1 to 6 carbon atoms or a cycloalkyl group having from 3 to 6 carbon atoms, (b) isolating a reaction product from step (a) and
(c) treating the isolated reaction product from step (b) without adding an additional solvent or after adding an additional solvent in the absence of any added alcohol, with hydrochloric acid or sulfuric acid to convert a 3-alkoxy-3-phenylpropionic acid ester of a formula (IV):

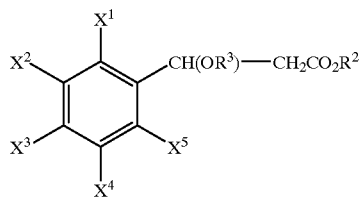
(IV)

wherein
X$^1$, X$^2$, X$^3$, X$^4$, X$^5$ and R$^2$ are as defined above and
R$^3$ represents an alkyl group having from 1 to 6 carbon atoms or a cycloalkyl group having from 3 to 6 carbon atoms, which is present in the reaction product, into a cinnamic acid ester of the formula (III).

2. A process according to claim 1 wherein X$^1$, X$^2$, X$^3$, X$^4$ and X$^5$ are the same as or different from each other and each represents a hydrogen atom, an alkyl group having from 1 to 6 carbon atoms, a halogen atom or an alkoxy group having from 1 to 6 carbon atoms.

3. A process according to claim 1, wherein X$^1$, X$^2$, X$^3$, X$^4$ and X$^5$ each represents a hydrogen atom.

4. A process according to claim 1, wherein the base is a metal alkoxide of formula (V):

R$^4$OM (V)

wherein R$^4$ represents an alkyl group having from 1 to 6 carbon atoms and M represents an alkali metal.

5. A process according to claim 4, wherein the metal alkoxide is a sodium alkoxide.

6. A process according to claim 4, wherein the metal alkoxide is sodium methoxide or sodium ethoxide.

7. A process according to claim 4, wherein the metal alkoxide is sodium methoxide.

8. A process according to claim 1, wherein the acid is sulfuric acid.

9. A process according to claim 1, wherein the reaction product contains a cinnamic acid and is subsequently reacted with an alcohol in the presence of an acid to convert said cinnamic acid to a cinnamic acid ester of formula (III).

10. A process according to claim 4, wherein X$^1$, X$^2$, X$^3$, X$^4$ and X$^5$ each represents a hydrogen atom.

11. A process according to claim 10, wherein the metal alkoxide is sodium methoxide or sodium ethoxide.

12. A process according to claim 10, wherein the metal alkoxide is sodium methoxide.

13. A process according to claim 10, wherein the reaction product contains a cinnamic acid and is subsequently reacted with an alcohol in the presence of an acid to convert said cinnamic acid to a cinnamic acid ester of formula (III).

14. A process according to claim 10, wherein the acid is sulfuric acid.

15. A process according to claim 13, wherein the acid is sulfuric acid.

16. A process according to claim 10, wherein the metal alkoxide is a sodium alkoxide.

17. A process according to claim 16, wherein the acid is sulfuric acid.

18. A process according to claim 17, wherein the reaction product contains a cinnamic acid and is subsequently reacted with an alcohol in the presence of an acid to convert said cinnamic acid to a cinnamic acid ester of formula (III).

19. A process according to claim 18, wherein the metal alkoxide is sodium methoxide or sodium ethoxide.

20. A process according to claim 4, wherein the metal alkoxide is in an amount of 0.5 to 10 equivalents relative to the benzaldehyde; step (a) is carried out at a temperature of −70° C. to 150° C. for 30 minutes to 48 hours; in step (c), the acid is in an amount of 0.1 to 20 equivalents per equivalent of the 3-alkoxy-3-phenylpropionic acid ester and step (c) is carried out at a temperature of 0 to 150° C. for 30 minutes to 48 hours.

* * * * *